(12) United States Patent
O'Brien

(10) Patent No.: US 7,786,856 B2
(45) Date of Patent: Aug. 31, 2010

(54) EXERCISE MONITOR

(76) Inventor: Conor O'Brien, 31 Raglan Road, Dublin 4 (IE)

( * ) Notice: Subject to any disclaimer, the term of this patent is extended or adjusted under 35 U.S.C. 154(b) by 465 days.

(21) Appl. No.: 10/599,752

(22) PCT Filed: Apr. 11, 2005

(86) PCT No.: PCT/EP2005/051591

§ 371 (c)(1),
(2), (4) Date: Jun. 1, 2007

(87) PCT Pub. No.: WO2005/098467

PCT Pub. Date: Oct. 20, 2005

(65) Prior Publication Data

US 2007/0275825 A1   Nov. 29, 2007

(30) Foreign Application Priority Data

Apr. 9, 2004   (EP) .................................. 04076087

(51) Int. Cl.
G08B 1/08   (2006.01)

(52) U.S. Cl. ................................. 340/539.11

(58) Field of Classification Search ............ 340/539.11, 340/573.1, 539.13, 691.6; 600/300, 520
See application file for complete search history.

(56) References Cited

U.S. PATENT DOCUMENTS

| 6,013,007 | A | 1/2000 | Root et al. |
| 6,251,048 | B1 * | 6/2001 | Kaufman ........................ 482/8 |
| 6,582,342 | B2 * | 6/2003 | Kaufman ........................ 482/8 |
| 6,736,759 | B1 * | 5/2004 | Stubbs et al. .................. 482/8 |
| 6,921,351 | B1 * | 7/2005 | Hickman et al. ............... 482/8 |
| 7,454,002 | B1 * | 11/2008 | Gardner et al. ......... 379/201.05 |
| 2002/0028730 | A1 * | 3/2002 | Kaufman ........................ 482/8 |
| 2003/0163283 | A1 | 8/2003 | O'Brien |
| 2003/0214432 | A1 | 11/2003 | Tawadrous et al. |
| 2005/0070809 | A1 * | 3/2005 | Acres ......................... 600/508 |

FOREIGN PATENT DOCUMENTS

| WO | WO 01/41879 A1 | 6/2001 |
| WO | WO 01/87426 A2 | 11/2001 |
| WO | WO 01/87426 A3 | 11/2001 |

OTHER PUBLICATIONS

PCT Search Report of the ISA for PCT/EP2005/051591; dated Dec. 2, 2005.

* cited by examiner

*Primary Examiner*—Phung Nguyen
(74) *Attorney, Agent, or Firm*—Daly, Crowley, Mofford & Durkee, LLP

(57) ABSTRACT

A device for measuring the aerobic capacity of a subject, has an input for receiving a measurement of distance travelled in a given time. The time is chosen to be sufficiently large to ensure that the user is working at the maximum of his or her aerobic capacity. A processor determines from the values of distance and time an aerobic capacity, and a measure of exercise level is output to the user based on the calculated aerobic capacity. The calculated aerobic capacity conforms to the relationship expressed as $VO2max = a + bx + c(x^2)$ wherein $VO2max$ is the maximal oxygen consumption of a user; a, b and c are non-zero constants, and x is a measure of distance per unit time.

16 Claims, 4 Drawing Sheets

EXERCISE MONITOR

CROSS REFERENCE TO RELATED APPLICATIONS

This application is a National Stage Application under 35 U.S.C. §371 of International Application number PCT/EP2005/051591 filed on Apr. 11, 2005, which was published in the English language on Oct. 20, 2005 as International Publication Number WO 2005/098467, and which claims the benefit under 35 U.S.C. §119(a) of European Patent Application 04076087.8, filed Apr. 9, 2004.

TECHNICAL FIELD

This invention relates to the monitoring of exercise levels and to devices, systems, and methods for use in exercise monitoring.

BACKGROUND ART

WO 01/69179 describes a device for attachment to the shoe of a user, which measures footfalls and thereby calculates the distance run or walked by the wearer of the device, to determine a level of exercise by the wearer of the device. This document also describes the prescription of exercise levels according to a percentage of a subject's aerobic capacity (maximal VO2 or VO2 max), with the capacity being determined as a constant (known as Cooper's constant) multiplied by the distance a subject can run in 12 minutes.

Polar Electro of Kempele, Finland produce an exercise monitor sold as the S625X running computer, which is proposed to operate in conjunction with the Nokia 5140 mobile phone (from Nokia Corporation). As described at http://www.polar.fi/mobileconnectivity/, the running computer receives data from a foot-worn pedometer to calculate distance travelled, and receives heart rate information from a chest-worn heart monitor. Instantaneous and cumulative data are displayed on the wristwatch style running computer.

After the session is complete the running computer can connect via infrared with a Nokia 5140 phone runs a software application to calculate and display statistics for the exercise session. The phone can also connect with another phone (via SMS message) to share the data, or to a personal computer (via infrared) to insert the session statistics into a training spreadsheet from which updated training goals are calculated. This data can also be sent to a web service for similar purposes.

Both WO 01/69179 and the Nokia/Polar devices rely on foot-worn and/or chest-worn units to measure evidence of exercise activity. The alternative to such measuring devices is to conduct laboratory or clinic sessions with dedicated treadmills, electrocardiograms and lung volume measurement apparatuses to obtain data resulting directly from the exercise activity.

One shortcoming in particular of the Polar/Nokia combination is the reliance on heart rate monitoring. Targeting exercise levels at a particular cardiac rate is useful in some instances but has serious drawbacks for groups of users who do not fit the standard heart rate/exercise response profile. Such users include cardiac patients, elite athletes, post-menopausal women, diabetics, and users who are targeting a weight loss goal as opposed to a fitness goal.

DISCLOSURE OF INVENTION

In a first aspect the invention provides a device for measuring the aerobic capacity of a subject, the device comprising input means for receiving a measurement of distance travelled by a user in a given time, said time being sufficiently large to ensure that the user is working at the maximum of his or her aerobic capacity, a processor for determining from said values of distance and time an aerobic capacity, and output means for outputting a measure of exercise level to the user based on the calculated aerobic capacity, wherein the aerobic capacity conforms to the relationship expressed as:

$$VO2max = a + bx + c(x^2)$$

wherein VO2max is the maximal oxygen consumption of a user,
wherein a, b and c are non-zero constants, and
wherein x is a measure of distance per unit time.

It will be appreciated that providing maximal oxygen output as a polynomial function of speed is fundamentally different from the method disclosed in WO 01/69179 which proposed providing VO2max as a multiple of the distance travelled in 12 miles based on Cooper's constant.

It has been found that the polynomial function provides a more accurate measurement of a user's functional capacity, allowing exercise levels to be subsequently prescribed as a proportion of the user's functional capacity.

Preferably, VO2max is expressed in milliliters of oxygen per kg bodyweight of the user per minute, x is a measure of the speed expressed as the distance run (in miles) in a time period of 12 minutes, and the constants a, b and c are in the following ranges:

$$2.2 \leq a \leq 3.4$$

$$20 \leq b \leq 27$$

$$2.0 \leq c \leq 2.9$$

Thus, where a user runs at a speed of 15 km/h, this equates to a 12 minute run of 3 km or 1.86 miles, giving a value of 1.86 for x in the above polynomial.

More preferably, the constants a, b and c are in the following ranges:

$$2.4 \leq a \leq 3.2$$

$$22 \leq b \leq 25$$

$$2.2 \leq c \leq 2.7$$

In a more preferred configuration, the constants a, b and c are in the following ranges:

$$2.7 \leq a \leq 2.9$$

$$23 \leq b \leq 24$$

$$2.4 \leq c \leq 2.5$$

Most preferably, a is approximately 2.8, b is approximately 23.44 and c is approximately 2.46

In preferred embodiments, the processor is also capable of calculating, from the previously determined aerobic capacity of the user, a speed target or target range equivalent to a proportion of the user's aerobic capacity, and dynamically outputting the current speed with an indication of the proximity of the current speed to the target speed or target speed range.

This enables a user to exercise at a level which is a set proportion of the functional capacity of that user. Thus, a user may decide or be advised to exercise at e.g. 75-80% of his or her functional capacity speed, and if that speed was previously determined to be e.g. 15 km/h then the device will provide an indication of whether or not the current speed is inside or outside the target range of 11.25 to 12 km/h.

In another aspect of the invention there is provided a system for measuring an exercise level of a user, the system comprising a global positioning system (GPS) module for measuring a geographical location of a user or a speed of a user, and a mobile telecommunications device having an active communication link, in use, with the GPS module, the mobile telecommunications device being updated regularly with the position of or speed of the GPS module, and the mobile telecommunications device being provided with computer program means for calculating, from said position or speed, an exercise level of the user in terms of aerobic capacity.

While it might be conjectured that the use of a GPS unit is an obvious equivalent to a pedometer based distance measurement system, this is not in fact the case. In the art of exercise measurement, the skilled person is conditioned by experience to rely only on evidence of actual exercise, such as heart rate or number of footfalls. A GPS system cannot provide any direct evidence of actual exercise, only of distance travelled, and accordingly would not normally be considered suitable for measuring exercise levels.

Indeed, this prejudice is supported by the fact that in the system proposed by Nokia and Polar, the telephone model supports a GPS-enabled accessory cover, but there was nevertheless a perceived necessity to employ a pedometer to measure the amount of exercise. In other words, the prejudice within the art of exercise monitoring meant that the possible use of the GPS measurements alone (which were inherently available to the phone) was overlooked.

An additional difference relative to the Polar/Nokia system is that the telecommunications device provides real time display and monitoring of exercise levels according to the present invention. In the Polar/Nokia system, the exercise data is retained in the running computer and only optionally transferred by IR link after the exercise session. This latter system precludes a real time interaction between the user and a monitoring site during the exercise session.

In contrast the fact that the telecommunications device of the present invention is supplied with the exercise data as exercise occurs means that it can continuously upload this data to a remote site allowing for a supervisor at that remote site to monitor the exercise session and provide feedback. Alternatively, the telecommunications device can be commanded or configured to send exercise data to a remote site using the telecommunications capabilities of the device at the conclusion of an exercise session. This allows data to be sent from the field and the exercise goals of the user to be updated immediately, or allows a supervisor to provide remote coaching feedback immediately to the user of the system.

Accordingly the system preferably also comprises a remote monitoring computer in communication with the telecommunications device, said computer being adapted to receive and process exercise data received from said telecommunications device over a mobile telecommunications network accessed by the telecommunications device.

The GPS module according to the invention may be integral to the telecommunications device, may be provided as an accessory for the device, or may be a separate GPS unit sharing a compatible communications link with the device.

In respect of each aspect of the invention referred to above, the invention also encompasses equivalent methods and computer programs for implementing such methods.

BRIEF DESCRIPTION OF THE DRAWINGS

The invention will now be further illustrated by the following description of embodiments thereof, given by way of example only with reference to the accompanying drawings, in which.

DETAILED DESCRIPTION OF PREFERRED EMBODIMENTS

Figure 1:
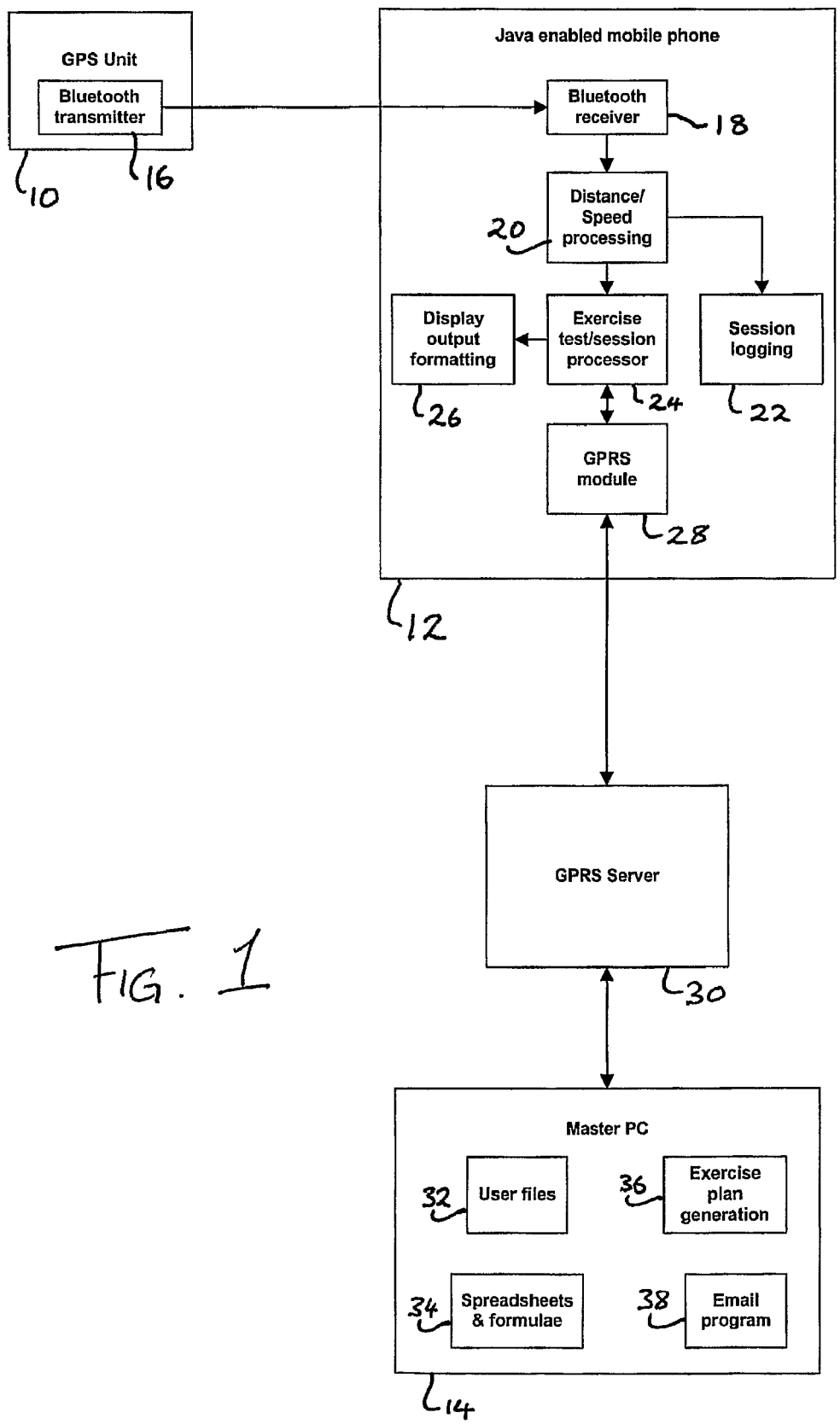
FIG. 1 is a functional block diagram of a system for measuring exercise levels.

Referring to FIG. 1, there is illustrated a functional block diagram of a system according to the present invention. The system comprises a GPS module 10, a mobile phone 12, and a personal computer 14.

GPS module 12 is a bluetooth-enabled unit which calculates position (latitude and longitude) in known manner from an array of satellites, and which connects by the bluetooth communications standard with other bluetooth-enabled devices. A suitable GPS module 12 is the "CRUX-II/BTGPS" (Trade Mark) GPS Receiver available from EMTAC Technology Corp of Hsinchu, Taiwan. Full details of this device are available at http://www.emtac.com/products/bluetooth/datasheet_btgps.html The mobile telecommunications device is a programmable mobile phone or personal digital assistant (PDA) having mobile telephony capabilities. As an example, the Communicator (Trade Mark) mobile phone available from Nokia Corporation may be used.

The GPS unit may provide positional information only or may provide instantaneous velocity data. In cases where it provides only positional information this is transmitted by a bluetooth transmitter 16 in the GPS unit to a GPS receiver 18 in the phone 14.

The phone carries out distance/speed processing to convert the GPS positional information into useful velocity information in order to establish either the instantaneous velocity or the distance travelled.

As an example, the GPS data may be transmitted in frames according to the GGA or RMC frame standards. The positional information is provided as numerical values for longitude, latitude and height.

The distance/speed processing unit calculates:

Location (Lat/Long)

1. This data can be read from either the GGA or the RMC frames. The latitude should be displayed in a format similar to dd°mm' ss.ssss N. or S. for and ddd° mm' ss.ssss E. or W. longitude. The equation for the conversion is as follows:-assume that latitude and longitude are of type float.

$$deg = (int)longitude/60;$$

$$min = (int)(longitude - deg*100);$$

$$sec = (longitude - deg*100 - min)*60;$$

Distance travelled since start of active session.
1. Degrees to radians divide latitude or longitude by 100 to give degrees (drop remainder)
2. Take remainder of above divide by 60 give a fraction of a degree.
3. Add 1&2 to get degrees. Divide by 180 and multiply by Pi to get angles in radians.

latitude and longitude in radians.

$$y=lat*6370950 \text{ if north}$$

$$y=-lat*6370950 \text{ if south}$$

$$x=long*6370950*cos(lat); \text{ if east}$$

$$x=-long*6370950*cos(lat); \text{ if west}$$

$$d=sqrt((x1-x2)^2+(y1-y2)^2);$$

The distance is calculated incrementally from the last position fix, and the update frequency can be chosen as desired. It has been found that an update frequency of 1 second is sufficiently frequent to record the distance travelled accurately.

Thus, for example, a runner running a circular course would carry a GPS unit transmitting positional data every second. A set of positional data received at time t1 $\{x_{t1}, y_{t1}\}$ is stored in a buffer after conversion as above, and when the next positional data set $\{x_{t2}, y_{t2}\}$ is received at time t2, the distance travelled from time t1 to time t2 is determined using the trigonometric calculation:

$$\text{distance } (t1 \rightarrow t2) = SQRT((x_{t2}-x_{t1})^2 + (y_{t2}-y_{t1})^2)$$

A cumulative total of the distance travelled is maintained, with each new distance measurement being added, to thereby arrive at a distance travelled for the session.

Speed can be calculated instantaneously (e.g. from the last ten seconds of distance data) and/or for the entire session. Data can be logged to a session log 22.

If the GPS unit is more sophisticated and provides a velocity output, then many of these functions can be performed on board the GPS unit. It can transmit, on a per second basis, the instantaneous velocity, and from this the cumulative distance can be derived.

An example of measuring exercise levels will now be described with reference to FIG. 2. This is a flowchart of the steps taken by the system of FIG. 1 to calculate the functional aerobic capacity of a user in a novel manner.

The user launches a software application on the mobile phone, which implements the functional system of FIG. 1. The user is first prompted to input personal details 100 including:

Name
Age (Years)
Weight (Kg) (Stone and lbs could also be preferred)
Height (Meters) (Feet and inches could also be used if preferred)
Sex.

The user is then requested to (1) start the logging/measurement session, (2) exit, or (3) edit details.

The start session screen allows the user to choose from a normal exercise session, and a Cooper's test, which is selected in step 102 (to measure functional capacity).

The software checks that there is a bluetooth link between the receiver 18 and a transmitter 16 of a compatible GPS module, and begins receiving GPS frame data 104.

A cumulative distance measurement is set to zero, 106 and the start position is calculated, 108. A 12-minute countdown timer is then activated, 110 and the user is prompted to begin running.

GPS data is received at regular intervals and used to calculate the new position of the user, step 112. The distance from the previous position is calculated in step 114 and this is added to a cumulative distance register, step 116. If the countdown timer has not reached 12 minutes, the process loops back to step 112. In this way, the cumulative distance register is continually updated to provide a measurement, when the 12 minutes have expired, of the distance covered by the user. This distance is stored in step 120.

The distance x, as measured in (or converted to) miles is then converted in step 122, using a polynomial of the format $a+bx+cx^2$, to a VO2max value. The conversion is carried out (FIG. 1) by a session processor 24. This VO2max value in turn (or in a combined calculation) can be converted to metabolic equivalents or METs using the conversion formula 1 MET=3.5 ml/kg/min.

The mobile phone displays statistics of the test dynamically to the user according to the output of a formatting module 26 (FIG. 1) which interacts with the screen display driver (not shown) of the mobile phone 12.

In the most preferred embodiment, the constants a, b and c for use in the above polynomial are chosen as a=2.8, b=23.448 and c=2.463. This has been found to provide a far more realistic match between the actual functional capacity of a user and the distance that user can travel in 12 minutes, than the previously used method of calculating VO2max as a multiple (Cooper's constant) of the distance travelled. The constants can be varied from the above values while still adhering to a polynomial formula, but each of a, b and c is non-zero.

In step 124 the functional capacity (either in ml/kg/min or in METs) is stored for use in future sessions as described below.

In an optional enhancement of the system, the device then connects automatically, or at the prompting of the user, by means of a GPRS module 28 to a server 30, step 126. (It will be readily appreciated that other communications protocols including GSM, 3G, WAP, or any other suitable mobile telecommunication protocol can be used to implement an interaction with a remote computer.)

The results of the test, and optionally, all of the logged data, are uploaded to the GPRS server, step 128, which passes them to a master PC 14 which executes software to analyse the results of the exercise session and to provide user feedback. This PC 14 stores user files 32 for each user, and relies on spreadsheets and formulae 34, as well as expert human interaction, to generate exercise plans 36 for the user. The exercise plans can be sent back directly to the GPRS module 28 of the device for display on the screen of the device, step 130. They can also be sent to the user via an email program, together with other exercise advice.

In this way a physician, physiotherapist, sports coach or other advisor can monitor the functional capacity of the user, and/or analyse the minutiae of the training session, and then prescribe an exercise regime accordingly. For example, it might be felt that although a cardiac patient displays a good aerobic capacity she should be restrained from exercising as vigorously as she comfortably can, in which case the advisor might downgrade the level at which she is advised to exercise in the following week.

Figure 2:
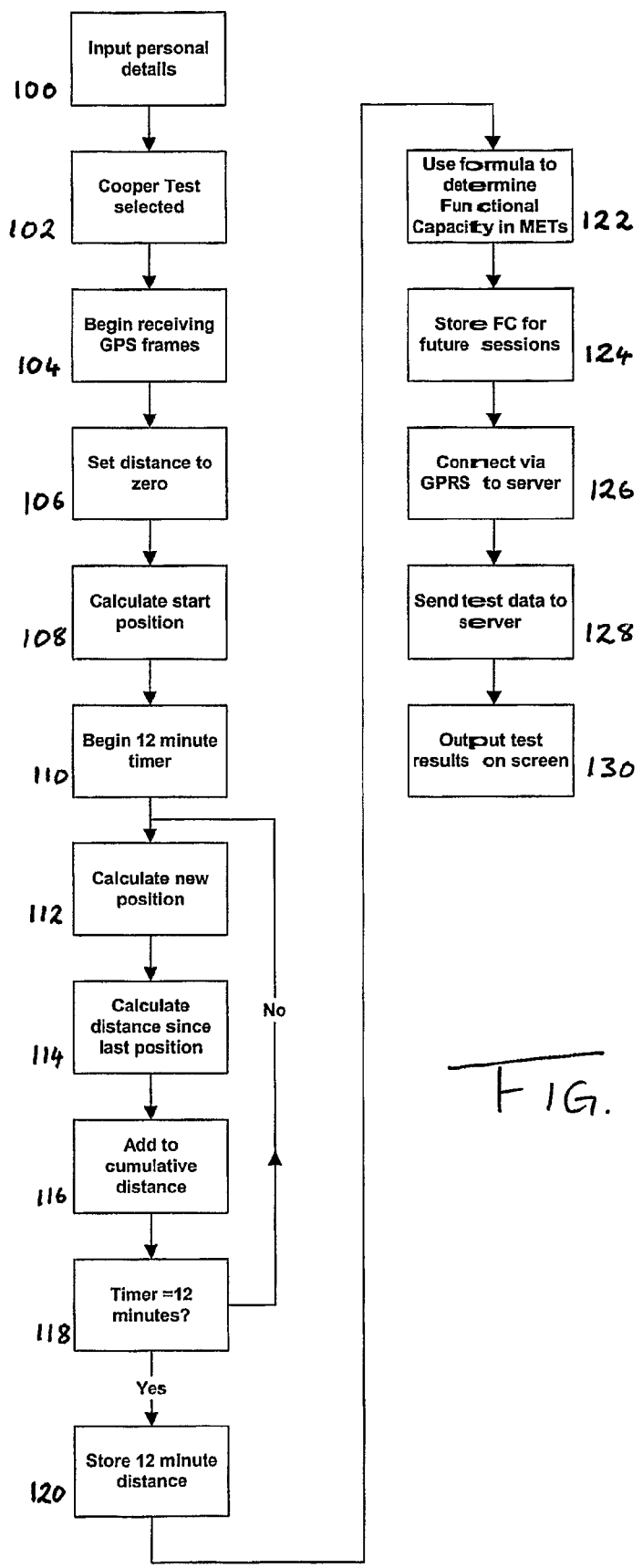
FIG. 2 is a flowchart illustrating the steps in measuring a functional aerobic capacity of a user with a system as in FIG. 1.
Figure 3:
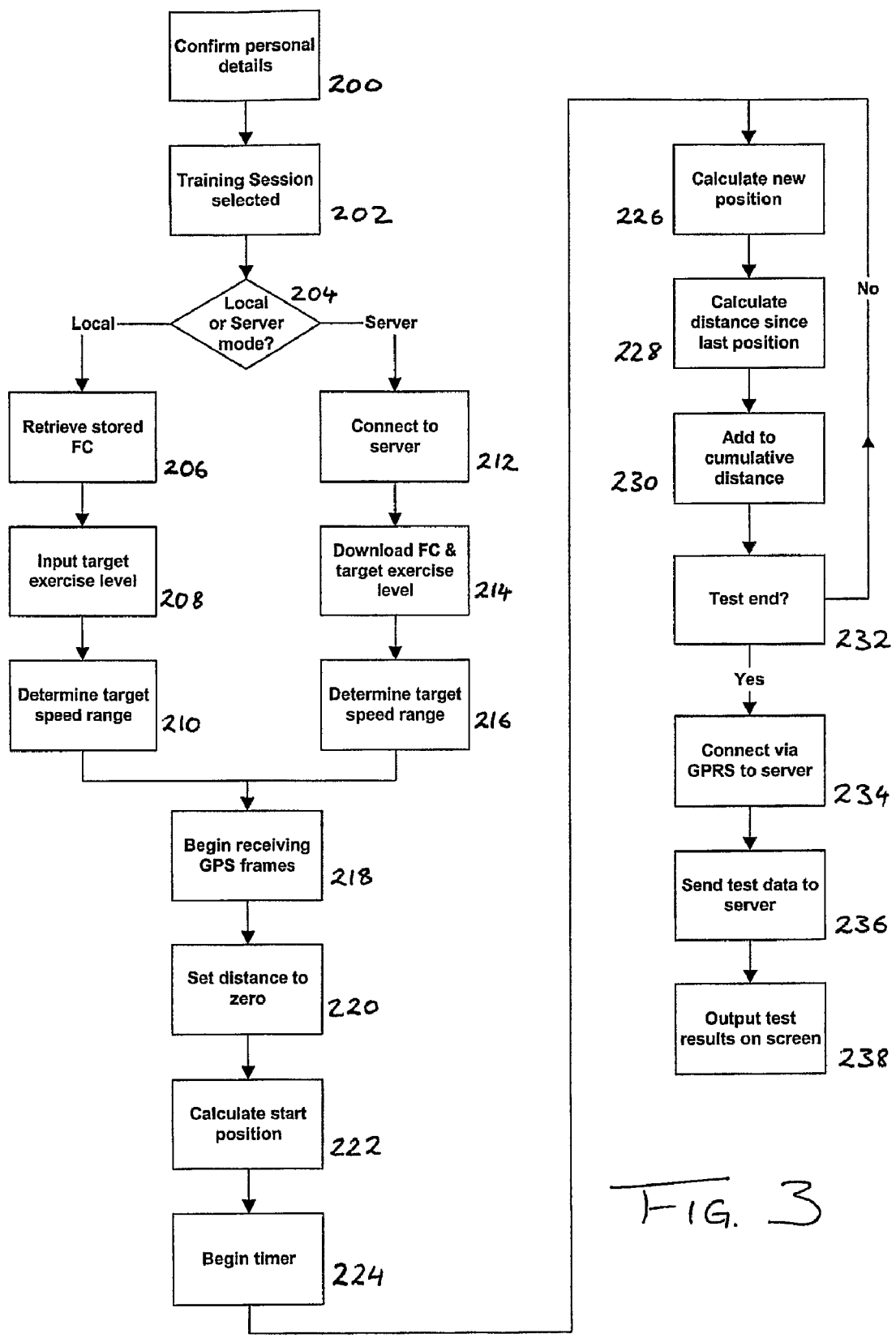
FIG. 3 is a flowchart illustrating the steps in subsequent monitoring and display of a user's exercise levels.

FIG. 3 illustrates the operation of the system in normal exercise session mode. Only those steps which are significantly different from those of FIG. 2 will be described in detail. When a user chooses a training session (as opposed to a Cooper's test), a decision 204 is made as to whether to use local or server mode. In local mode, the device retrieves the stored functional capacity or FC, step 206 (or the equivalent speed which was used to calculate the functional capacity) and the user is prompted to input a target exercise level 208 (or a previously input target level can be used. The target level is usually expressed as a percentage of FC, e.g. 60%, or a range such as 50-75% of FC.

If the user had previously demonstrated the ability to cover a distance of 2.2 miles in 12 minutes (a speed of 11 miles per hour) then the target speed range of 50-75% (say) of this is directly converted in terms of speed to a desired exercise rate of 5.5 to 8.25 miles per hour.

Where the device operates in server mode, it connects to the server using GPRS and requests a functional capacity (or equivalent speed) and a target exercise level, step 214, from which a target speed range is determined.

Of course these steps could be simplified and in server mode or local mode, one could simply have a stored target speed or speed range. However, this would not take into account changes in functional capacity, and hence in desired exercise levels, as functional capacity changes over time (which are derived using the device by periodically repeating the Cooper test or some other distance/FC test).

Once a target speed has been established in step 210 or 216, the device begins to calculate distance and speed using a series of steps 218-232 which mirror steps 104-118 of FIG. 2, with the main difference being that a 12 minute period is not specified in this instance and the user can set a different exercise period or can choose to end the test after a set distance has been covered for instance.

The output of the device can provide any suitable data which the user might want, including time elapsed, distance covered, speed as a percentage of functional capacity speed, exercise level expressed in METs, instantaneous speed in any convenient units, etc.

In the active mode the unit will preferably display:
Current speed.
Calories burned during session to date (calculated with reference to the speed and the weight of the user)
Maximum speed.
Duration of session.
The user will have the option to finish the session.

Again, when the test has ended the device can be made to connect (or can automatically connect) to a GPRS server connected to a master PC (steps 234-238) to upload session data and download exercise goals.

In the case of either FIG. 2 or FIG. 3, the device can be in dynamic communication with a master PC during the test itself to provide real time logging and analysis of the test data at a remote site, and to enable a remotely located coach or medical advisor to monitor and/or advise as the test progresses.

Figure 4:
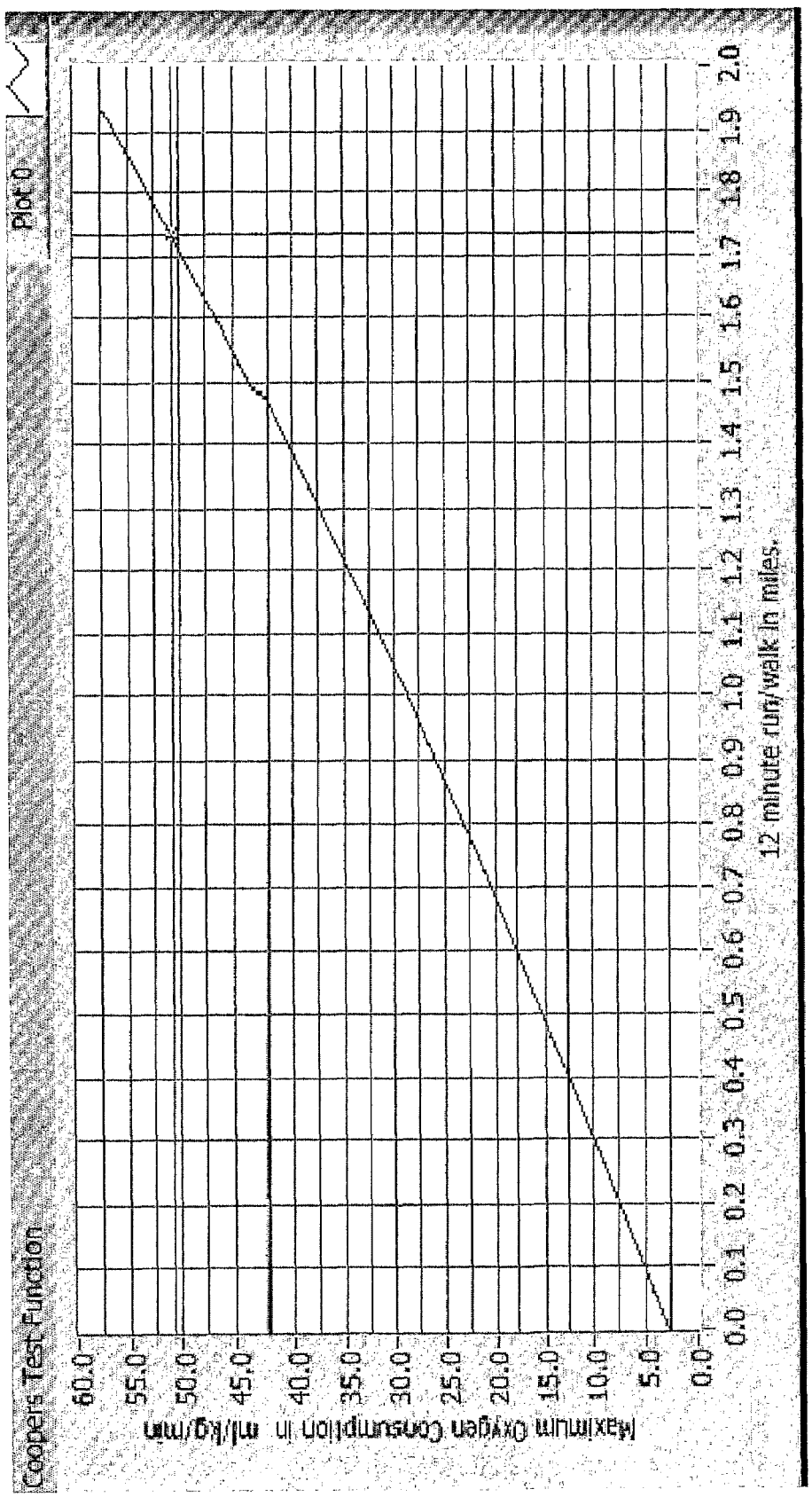
FIG. 4 is a graph illustrating a relationship between functional capacity (VO2max) and the average speed of a user expressed as the distance covered in a 12 minute walk or run.

FIG. 4 shows the preferred polynomial relationship between the distance covered In 12 miles (and thus speed) and the maximal aerobic capacity. Rather than defining the polynomial relationship in terms of the constants a, b and c, reference can be made to this graph and an alternative formulation of the invention can define the maximal oxygen capacity as a point on or close to the line shown in the graph for the equivalent speed achieved in a test of maximal capacity.

The invention claimed is:
1. A device for measuring the aerobic capacity of a subject, the device comprising input means for receiving a measurement of distance travelled by a user in a given time, said time being sufficiently large to ensure that the user is working at the maximum of his or her aerobic capacity, a processor for determining from said values of distance and time an aerobic capacity, and output means for outputting a measure of exercise level to the user based on the calculated aerobic capacity, wherein the aerobic capacity conforms to the relationship expressed as:

$$VO2max = a + bx + c(x^2)$$

wherein VO2max is the maximal oxygen consumption of a user,
wherein a, b and c are non-zero constants, and
wherein x is a measure of distance per unit time.

2. The device according to claim 1, wherein VO2max is expressed in milliliters of oxygen per kg bodyweight of the user per minute, x is a measure of the speed expressed as the distance run in miles in a time period of 12 minutes, and the constants a, b and c are in the following ranges:

$$2.2 \leq a \leq 3.4$$

$$20 \leq b \leq 27$$

$$2.0 \leq c \leq 2.9.$$

3. The device as claimed in claim 2, wherein the constants a, b and c are in the following ranges:

$$2.4 \leq a \leq 3.2$$

$$22 \leq b \leq 25$$

$$2.2 \leq c \leq 2.7.$$

4. The device as claimed in claim 3, wherein the constants a, b and c are in the following ranges:

$$2.7 \leq a \leq 2.9$$

$$23 < b \leq 24$$

$$2.4 \leq c \leq 2.5.$$

5. The device as claimed in claim 4, wherein a is approximately 2.8, b is approximately 23.44 and c is approximately 2.46.

6. The device as claimed in any preceding claim, wherein the processor is also capable of calculating, from the previously determined aerobic capacity of the user, a speed target or target range equivalent to a proportion of the user's aerobic capacity, and dynamically outputting the current speed with an indication of the proximity of the current speed to the target speed or target speed range.

7. A method of measuring the aerobic capacity of a subject, comprising the steps of:
receiving a measurement of distance travelled by a user in a given time, said time being sufficiently large to ensure that the user is working at the maximum of his or her aerobic capacity,
determining from said values of distance and time an aerobic capacity, and
outputting a measure of exercise level to the user based on the calculated aerobic capacity,
wherein the aerobic capacity conforms to the relationship expressed as:

$$VO2max = a + bx + c(x^2)$$

wherein VO2max is the maximal oxygen consumption of a user,
wherein a, b and c are non-zero constants, and
wherein x is a measure of distance per unit time.

8. A computer-readable storage medium having computer-readable code thereon, comprising instructions, which when executed in a computing device are effective to cause the computing device to measure an exercise level of a user by carrying out the steps of:

receiving a measurement of distance travelled by a user in a given time, said time being sufficiently large to ensure that the user is working at the maximum of his or her aerobic capacity, determining from said values of distance and time an aerobic capacity, and outputting a measure of exercise level to the user based on the calculated aerobic capacity, wherein the aerobic capacity conforms to the relationship expressed as:

$$VO2\max = a + bx + c(x^2)$$

wherein VO2max is the maximal oxygen consumption of a user, wherein a, b and c are non-zero constants, and wherein x is a measure of distance per unit time.

9. The computer-readable storage medium as claimed in claim 8, wherein the computing device comprises a mobile telecommunications device, wherein the computer-readable storage medium comprises at least one of a piece of software installed on the computer-readable storage medium, or a piece of software downloaded to the computer-readable medium.

10. A system for measuring an exercise level of a user, the system comprising a global positioning system (GPS) module for measuring a geographical location of a user or a speed of a user, and a mobile telecommunications device having an active communication link, in use, with the GPS module, the mobile telecommunications device being updated regularly with the position of or speed of the GPS module, and the mobile telecommunications device being provided with computer program means for calculating, from said position or speed, an exercise level of the user in terms of aerobic capacity, wherein the aerobic capacity conforms to the relationship expressed as:

$$VO2\max = a + bx + c(x^2)$$

wherein VO2max is the maximal oxygen consumption of a user, wherein a, b and c are non-zero constants, and wherein x is a measure of distance per unit time.

11. The system as claimed in claim 10, further comprising a remote monitoring computer in communication with the telecommunications device, said computer being adapted to receive and process exercise data received from said telecommunications device over a mobile telecommunications network accessed by the telecommunications device.

12. The system as claimed in claim 10 or 11, wherein the GPS module is integral to the telecommunications device.

13. The system as claimed in claim 10 or 11, wherein the GPS module is provided as an accessory for the telecommunications device.

14. The system as claimed in claim 10 or 11, wherein the GPS module is a separate GPS unit sharing a compatible communications link with the telecommunications device.

15. A method of measuring an exercise level of a user, the method comprising the steps of:

measuring a geographical location of a user or a speed of a user using a global positioning system (GPS) module, regularly updating a mobile telecommunications device with the position of or speed of the GPS module, calculating, from said position or speed, an exercise level of the user in terms of aerobic capacity, wherein the aerobic capacity conforms to the relationship expressed as:

$$VO2\max = a + bx + c(x^2)$$

wherein VO2max is the maximal oxygen consumption of a user, wherein a, b and c are non-zero constants, and wherein x is a measure of distance per unit time.

16. A computer-readable storage medium having computer-readable code thereon, comprising instructions, which when executed in a computing device are effective to cause the computing device to measure an exercise level of a user by carrying out the steps of:

receiving data indicative of the speed or position of a user using a global positioning system (GPS) module, and calculating, from said position or speed, an exercise level of the user in terms of aerobic capacity, wherein the aerobic capacity conforms to the relationship expressed as:

$$VO2\max = a + bx + c(x^2)$$

wherein VO2max is the maximal oxygen consumption of a user, wherein a, b and c are non-zero constants, and wherein x is a measure of distance per unit time.

\* \* \* \* \*